United States Patent [19]

Uphues et al.

[11] Patent Number: 5,442,082
[45] Date of Patent: Aug. 15, 1995

[54] ALKOXYLATED COMPOUNDS PRODUCED FORM EPOXIDIZED CARBOXYLIC ACID DERIVATIVES

[75] Inventors: Guenter Uphues, Monheim; Uwe Ploog, Haan; Peter Daute, Essen; Gerhard Stoll, Korschenbroich; Berthold Schreck, Duesseldorf, all of Germany

[73] Assignee: Henkel Kommanditgesellschaft auf Aktien, Duesseldorf, Germany

[21] Appl. No.: 357,559

[22] Filed: Dec. 16, 1994

Related U.S. Application Data

[63] Continuation of Ser. No. 915,729, Jul. 27, 1992, abandoned.

[30] Foreign Application Priority Data

Jan. 26, 1990 [DE] Germany ............... 40 02 213.7

[51] Int. Cl.$^6$ ............................................. C07C 69/96
[52] U.S. Cl. .................................... 554/149; 554/213; 162/5
[58] Field of Search ................. 554/149, 213; 162/5

[56] References Cited

U.S. PATENT DOCUMENTS

| | | | |
|---|---|---|---|
| 3,337,595 | 8/1967 | Lamount | 554/149 |
| 3,663,583 | 5/1972 | Haynes | 260/410 |
| 3,859,318 | 1/1975 | Lesuer et al. | 554/149 |
| 4,022,808 | 5/1978 | Yoshihara et al. | 554/149 |
| 4,115,415 | 9/1978 | Yoshihara et al. | 260/140 |
| 4,124,609 | 11/1978 | Bilyk | 260/406 |
| 4,586,982 | 5/1986 | Poppel | 162/5 |
| 4,612,192 | 9/1986 | Scheuffgen | 424/70 |
| 5,100,574 | 3/1992 | Urushibata et al. | 252/174.22 |
| 5,164,124 | 11/1992 | Lange et al. | 554/149 |
| 5,221,433 | 6/1993 | Daute et al. | 162/5 |
| 5,223,089 | 6/1993 | Kato | 162/5 |
| 5,237,080 | 8/1993 | Daute et al. | 554/213 |

FOREIGN PATENT DOCUMENTS

| | | |
|---|---|---|
| 0067333 | 12/1982 | European Pat. Off. . |
| 0335295 | 10/1989 | European Pat. Off. . |
| 857364 | 10/1952 | Germany . |
| 3118192 | 11/1982 | Germany . |
| 3318596 | 11/1984 | Germany . |
| 3839479 | 6/1990 | Germany . |

*Primary Examiner*—José G. Dees
*Assistant Examiner*—Samuel Barts
*Attorney, Agent, or Firm*—Ernest G. Szoke; Wayne C. Jaeschke; Real J. Grandmaison

[57] ABSTRACT

The invention relates to alkoxylated compounds prepared by reaction of epoxidized $C_{10-22}$ carboxylic acid derivatives with $C_{2-4}$ alkylene oxides in the presence of alkoxylation catalysts and mono- and/or polyhydric alcohols.

20 Claims, No Drawings

ALKOXYLATED COMPOUNDS PRODUCED FORM EPOXIDIZED CARBOXYLIC ACID DERIVATIVES

This application is a continuation of application Ser. No. 07/915,729, filed on Jul. 27, 1992, now abandoned, which was filed under 35 USC 371 of application PCTEP9100084.

BACKGROUND OF THE INVENTION AND FIELD OF THE INVENTION

This invention relates to alkoxylated compounds of epoxidized $C_{10-22}$ carboxylic acid derivatives, to a process for their production and to the use of these alkoxylated compounds.

DISCUSSION OF RELATED ART

Ethoxylated and/or propoxylated castor oils are used, for example, in cosmetic preparations, detergents or lubricating oils or as antistatic agents for nylon carpets (Kirk-Othmer: Encyclopedia of Chemical Technology, Vol. page 9, John Wiley, New York (1979)). However, the disadvantage of using ethoxylated and/or propoxylated castor oils is that the quantities of castor oil available on the market and hence the quantities of ethoxylated and/or propoxylated castor oils are subject to considerable fluctuations. Poor harvests in the main areas of cultivation, namely Brazil and India, result in a shortage of the starting material, castor oil, at more or less long intervals. Accordingly, there is a need for an equivalent substitute for alkoxylated castor oils. Above all, the substitute should be accessible from a broader and less crisis-prone raw material base and should be ecologically and toxicologically safe.

DESCRIPTION OF THE INVENTION

It has now been found that epoxidized $C_{10-22}$ carboxylic acid derivatives which have been reacted with $C_{2-4}$ alkylene oxides in the presence of alkoxylation catalysts and mono- and/or polyhydric alcohols can be used as a substitute for alkoxylated castor oils.

Accordingly, the present invention relates to alkoxylated compounds prepared by reaction of epoxidized $C_{10-22}$ carboxylic acid derivatives with $C_{2-4}$ alkylene oxides in the presence of alkoxylation catalysts and mono- and/or polyhydric alcohols.

The present invention also relates to a process for the production of alkoxylated compounds, characterized in that epoxidized $C_{10-22}$ carboxylic acid derivatives are reacted with $C_{2-4}$ alkylene oxides in the presence of alkoxylation catalysts and mono- and/or polyhydric alcohols at temperatures in the range from 110° to 220° C. and under pressures of $10^5$ to $2 \cdot 10^6$ Pa.

The alkoxylated compounds according to the invention are produced by conventional organic synthesis methods, namely by reaction of epoxidized $C_{10-22}$ carboxylic acid derivatives with $C_{2-4}$ alkylene oxides in the presence of alkoxylation catalysts, for example sodium methylate and/or potassium hydroxide, and mono- and/or polyhydric alcohols at temperatures of preferably 150° to 190° C. and under pressures of preferably $3 \cdot 10^5$ to $9 \cdot 10^5$ Pa. The alkylene oxides are used in such quantities that the alkylene oxide content of the alkoxylated compounds obtained is preferably between 20 and 90% by weight and more preferably between 40 and 80% by weight. Ethylene oxide and/or propylene oxide are preferably used as the $C_{2-4}$ alkylene oxides. Where ethylene oxide and propylene oxide are used, the two alkylene oxides may be added to the reaction mixture simultaneously or in succession. The mono- and/or polyhydric alcohols are preferably used in quantities of 0.1 to 2.0% by weight and more preferably in quantities of 0.2 to 1.0% by weight, based on one epoxide group. Suitable mono- and/or polyhydric alcohols are linear and/or branched $C_{1-18}$ alkyl alcohols, for example methanol, ethanol and/or stearyl alcohol, optionally alkoxylated with 1 to 30 mol $C_{2-4}$ alkylene oxide units, linear and/or branched alkanediols, for example ethylene glycol, propane-1,2-diol, propane-1,3-diol, butane-1,4-diol, hexane-1,6-diol and/or dodecane-1,12-diol, optionally alkoxylated with 1 to 30 mol $C_{2-4}$ alkylene oxide units, glycerol, diglycerol, polyglycerol, trimethylol propane, pentaerythritol and/or sugar alcohols, such as mannitol and/or sorbitol.

The epoxidized $C_{10-22}$ carboxylic acid derivatives used as educts for the production of the alkoxylated compounds according to the invention can be obtained by epoxidation of unsaturated $C_{10-22}$ carboxylic acid derivatives. According to DE-PS 857 364, unsaturated carboxylic acid derivatives can be epoxidized by reaction with peracetic acid in the presence of acidic catalysts or with performic acid formed in situ from formic acid and hydrogen peroxide. The iodine values of the epoxidation products obtained are below 20 and preferably below 15. Suitable unsaturated carboxylic acid derivatives are any OH-group-free, naturally occurring and/or synthesizable carboxylic acid derivatives containing carboxylic acid residues with at least one or two double bonds in the 9- and/or 13-position, for example 9c-dodecenoic acid, 9c-tetradecenoic acid, 9c-hexadecenoic acid, 9c-octadecenoic acid, 9t-octadecenoic acid, 9c,12c-octadecadienoic acid, 9c,12c,15c-octadecatrienoic acid, 9c-eicosenoic acid and/or 13c-docosenoic acid derivatives and/or mixtures having at least a high content of such unsaturated carboxylic acid derivatives. Unsaturated carboxylic acid derivatives containing $CC_{16-22}$ carboxylic acid residues with at least one or two double bonds in the 9- and/or 13-position, are preferred. Suitable unsaturated carboxylic acid derivatives are, for example, unsaturated $C_{10-22}$ a carboxylic acid esters, unsaturated $C_{10-22}$ carboxylic acid amides, unsaturated $C_{10-22}$ carboxylic acid mono- and/or di-$C_{1-4}$-alkyl amides and/or unsaturated $C_{10-22}$ carboxylic acid mono- and/or -di-$C_{1-4}$ alkanolamides. Unsaturated $C_{10-22}$ carboxylic acid alkyl esters containing 1 to 18 C atoms in the monohydric alcohol component and/or mono-, di- and/or triglycerides containing $C_{10-22}$ carboxylic acid residues with at least one or two double bonds in the 9- and/or 13-position are preferred.

Examples of unsaturated $C_{10-22}$ carboxylic acid $C_{1-18}$ alkyl esters, which may be obtained in known manner by esterification of the corresponding unsaturated carboxylic acids or by transesterification of the corresponding mono-, di- and/or triglycerides with $C_{1-18}$ alkyl alcohols, for example methanol, ethanol, propanal, butanol, isobutanol, 2-ethyl hexanol, decanol and/or stearyl alcohol, are palmitoleic acid methyl ester, oleic acid methyl ester, oleic acid ethyl ester, oleic acid isobutyl ester, oleic acid 2-ethyl hexyl ester and/or oleic acid decyl ester and/or $C_{10-22}$ carboxylic acid $C_{1-18}$ alkyl ester mixtures having at least a high content of $C_{10-22}$ carboxylic acid $C_{1-18}$ alkyl esters containing at least one or two double bonds in the 9- and/or 13-position in the carboxylic acid residues, such as palm oil fatty acid methyl ester, soybean oil fatty acid methyl ester, soybean oil fatty acid 2-ethyl hexyl ester, rapeseed oil fatty acid methyl ester and/or tallow fatty acid ethyl ester. Particularly suitable mono-, di- and/or triglycerides containing OH-group-free, unsaturated $C_{10-22}$ carboxylic acid residues with at least one or two double bonds in the 9- and/or 13-position are fats and/or oils of natural origin, of which the carboxylic acid content is mainly made up of unsaturated $C_{10-22}$ carboxylic acids with at least one or two double bonds in the 9- and/or 13-position, preferably mainly of unsaturated $C_{16-22}$ carboxylic acids with at least one or two double bonds in the 9- and/or 13-position, such as olive oil, linseed oil, sunflower oil, safflower oil, soybean oil, peanut oil, cottonseed oil, high-erucic and/or low-erucic rapeseed oil, palm oil, lard and/or tallow.

The alkoxylated compounds according to the invention are suitable for the removal of printing inks from printed wastepaper and/or paper circuit waters. Accordingly, the present invention also relates to the use of alkoxylated compounds prepared by reaction of epoxidized $C_{10-22}$ carboxylic acid derivatives with $C_{2-4}$ alkylene oxides in the presence of alkoxylation catalysts and mono- and/or polyhydric alcohols for the removal of printing inks from wastepaper and/or paper circuit waters.

The alkoxylated compounds according to the invention are preferably added to paper Stock suspensions in quantities of 0.02 to 2% by weight and more preferably in quantities of 0.1 to 0.8% by weight, based on air-dry paper stock. Air-dry paper stock means that an equilibrium state of internal moisture has been established in the paper stock. This equilibrium state depends on the temperature and relative humidity of the air.

In many cases, the deinking result, i.e. the removal of printing inks from printed wastepaper, can be improved if the alkoxylated compounds according to the invention are used in combination with, for example, $C_{10-22}$ fatty acids, such as Olinor®4010, Olinor®4020 and/or Olinor®DG40 (all products of Henkel KGaA), ethoxylated alkyl alcohols containing 6 to 22 carbon atoms, ethoxylated alkyl phenols; polymers, such as polyacrylamides and/or polydimethyl aminoethyl methacrylate, and/or copolymers, for example of the type described in DE 38 39 479. The total quantity of these optional constituents is between 0.1 and 1% by weight, based on air-dry paper stock.

In the presence of the alkoxylated compounds according to the invention, water-dilutable and/or solvent-containing printing inks, for example rotary newsprint inks, book printing inks, offset printing inks, illustration intaglio printing inks, flexographic printing inks, laser printing inks and/or packaging intaglio printing inks, may be removed from printed wastepaper, for example newspapers, magazines, computer paper, journals, brochures, forms, telephone directories and/or catalogues. The wastepaper deinked in the presence of the alkoxylated compounds according to the invention is distinguished by very high degrees of whiteness.

Printed wastepaper is disintegrated at temperatures of 20° to 60° C. in a pulper in an aqueous solution preferably containing 0 to 1.5% by weight 100% hydrogen peroxide, 0 to 2.5% by weight 99% by weight NaOH, 0 to 4.0% by weight soda waterglass having a solids content of 35% by weight (37 to 40.Be), 0.02 to 2% by weight alkoxylated compounds according to the invention and 0 to 1% by weight of the optional constituents mentioned above—all percentages by weight are based on air-dry wastepaper—at pulp densities of, for example, 1 to 5% by weight. The paper stock suspensions are then stirred into water or water is added to them so that 0.6 to 1.6% by weight paper stock suspensions are obtained. After a residence time of 60 to 120 minutes at temperatures in the range from 20° to 60° C., the detached printing ink particles are then removed from the fiber suspensions in known manner by washing or flotation (Ullmanns Enzyklopädie der technischen Chemie, 4th Edition, Vol. 17, pages 570 to 571 (1979)), preferably by flotation, for example in a Denver flotation cell.

Where the alkoxylated compounds according to the invention are used, printing inks are removed both from the wastepaper and from the circuit water. The compounds according to the invention may also be used for the separate treatment of paper circuit waters. In cases such as these, the printing ink particles are removed, for example by filtration or flotation, after the addition of 2 to 10 mg of the alkoxylated compounds according to the invention per liter circuit water.

EXAMPLES

EXAMPLE 1

156 g epoxidized soybean oil (approximate composition: 25% by weight oleic acid, 48% by weight linoleic acid, 7% by weight linolenic acid, 2% by weight stearic acid; epoxide content=6.3% by weight; iodine value=4; acid value=0.2), 4 g glycerol and 0.8 g of a 30% by weight methanolic sodium methylate solution were introduced into an autoclave. After removal of the methanol in vacuo, the reaction mixture was heated to 180° C. 240 g ethylene oxide were then added so that the pressure in the reactor did not exceed a value of $8 \cdot 10^5$ Pa. After 9 hours, the autoclave was evacuated and cooled to room temperature (20° C.) to remove any ethylene oxide still present. The liquid product obtained had an OH value (OHV) of 120, a saponification value (SV) of 74.4 and an epoxide content of 0.81% by weight.

EXAMPLE 2

As in Example 1, 300 g epoxidized soybean oil (characteristic data as in Example 1) were reacted with 700 g ethylene oxide for 6 hours at 180° C. in the presence of 20 g glycerol and 2.1 g of a 30% by weight methanolic sodium methylate solution. The liquid product obtained had an of 86, an SV of 51 and an epoxide content of 0.29% by weight.

EXAMPLE 3

As in Example 1, 390 g epoxidized soybean oil fatty acid 2-ethyl hexyl ester (fatty acid composition as in Example 1; epoxide content=4.99% by weight; SV=140.1) were reacted with 610 g ethylene oxide for 10 hours in the presence of 20 g glycerol and 2.1 g of a 30% by weight sodium methylate solution. The liquid product obtained had an OHV of 89, an SV of 53 and an epoxide content of 0.5% by weight.

Application Examples 98 g air-dry (=90 g bone-dry for 8% moisture) printed wastepaper consisting of 50% by weight newspapers and 50% by weight magazines were disintegrated for 10 minutes at 45° C. by dispersing disk in an aqueous solution containing 2.0% by weight soda waterglass, solids content 35% by weight (37–40.Be), 0.7% by weight hydrogen peroxide (100% by weight), 1.0% by weight sodium hydroxide (99% by weight) and 0.15% by weight alkoxylated compound according to the invention (all percentages by weight are based on air-dry paper stock) in a laboratory pulper at a pulp density of 3.5% by weight. The pulp was then diluted with water to 1% by weight pulp density, left standing for 1.75 hours at 45° C. and then subjected to flotation for 12 minutes at 45° C. in a Denver laboratory flotation cell at 1,900 revolutions per minute. After flotation, the pulp was separated from the water (circuit water) on a suction filter apparatus, formed into a sheet between two filter papers on a photo dry press and dried for 90 minutes at 100° C.

The deinking results are shown in Table 1. The deinkability value (DEM) was calculated from the reflection factors $R_{457\,nm}$ (whiteness) of the printed (BS), deinked (DS) and unprinted (US) paper stock in accordance with the following formula:

$$DEM(\%) = \frac{\text{whiteness }(DS) - \text{whiteness}(BS)}{\text{whiteness}(US) - \text{whiteness}(BS)} \times 100$$

(0% means no deinking, 100% means quantitative deinking).

The circuit water was clear in every case.

TABLE 1

| Alkoxylated compounds used, prepared in acc. with Example No. | $R_{457}$[1] (US) | $R_{457}$ (BS) | $R_{457}$ (DS) | DEM (%) |
| --- | --- | --- | --- | --- |
| 1 | 62 | 41 | 59 | 84 |
| 2 | 62 | 41 | 59 | 85 |
| 3 | 62 | 41 | 60 | 86 |

[1] $R_{457}$ means $R_{457\,nm}$

We claim:

1. An alkoxylated compound prepared by reacting an epoxidized $C_{10}$–$C_{22}$ carboxylic acid derivative with a $C_2$–$C_4$ alkylene oxide in the presence of an alkaline alkoxylation catalyst and a polyhydric alcohol.

2. An alkoxylated compound as in claim 1 containing from about 20 to about 90% by weight of said alkylene oxide, based on the weight of said alkoxylated compound.

3. An alkoxylated compound as in claim 1 wherein said alkylene oxide is selected from the group consisting of ethylene oxide and propylene oxide.

4. An alkoxylated compound as in claim 1 wherein said alcohol is present in an amount of about 0.1 to about 2% by weight per epoxide group.

5. An alkoxylated compound as in claim 1 wherein said epoxidized carboxylic acid derivative contains 16 to 22 carbon atoms.

6. An alkoxylated compound as in claim 1 wherein said epoxidized carboxylic acid derivative is selected from the group consisting of an epoxidized mono-, di- and triglyceride, and an epoxidized carboxylic acid alkyl ester containing 1 to 18 carbon atoms in the monohydric alcohol.

7. The process of preparing an alkoxylated compound comprising reacting an epoxidized $C_{10}$–$C_{22}$ carboxylic acid derivative with a $C_2$–$C_4$ alkylene oxide in the presence of an alkaline alkoxylation catalyst and a polyhydric alcohol at a temperature of from about 110° to about 220° C. and under a pressure of from about $10^5$ to $2\cdot10^6$ Pa.

8. A process as in claim 7 wherein said temperature is from about 150° to about 190° C. and said pressure is from about $3\cdot10^5$ Pa. to about $9\cdot10^5$ Pa.

9. A process as in claim 7 wherein said alkylene oxide is employed in an amount to provide an alkylene oxide content of from about 20 to about 90% by weight to said alkoxylated compound.

10. A process as in claim 7 wherein said alkylene oxide is selected from the group consisting of ethylene oxide and propylene oxide.

11. A process as in claim 7 wherein said alcohol is present in an amount of about 0.1 to about 2% by weight per epoxide group.

12. A process as in claim 7 wherein said epoxidized carboxylic acid derivative contains 16 to 22 carbon atoms.

13. A process as in claim 7 wherein said epoxidized carboxylic acid derivative is selected from the group consisting of an epoxidized mono-, di- and tri-glyceride, and an epoxidized carboxylic acid alkyl ester containing 1 to 18 carbon atoms in the monohydric alcohol.

14. The process of regenerating wastepaper containing printing ink comprising the steps of;
 (1) fiberizing said wastepaper in an aqueous alkaline deinking solution containing a deinking effective quantity of an alkoxylated compound prepared by reacting an epoxidized $C_{10}$–$C_{22}$ carboxylic acid derivative with a $C_2$–$C_4$ alkylene oxide in the presence of an alkaline alkoxylation catalyst and a polyhydric alcohol to detach ink particles from said wastepaper, and
 (2) removing the detached ink particles from the deinking solution.

15. A process as in claim 14 wherein said alkoxylated compound contains from about 20 to about 90% by weight of said. alkylene oxide, based on the weight of said alkoxylated compound.

16. A process as in claim 14 wherein said alkylene oxide is selected from the group consisting of ethylene oxide and propylene oxide.

17. A process as in claim 14 wherein said alcohol is present in an amount of about 0.1 to about 2% by weight per epoxide group.

18. A process as in claim 14 wherein said epoxidized carboxylic acid derivative contains 16 to 22 carbon atoms.

19. A process as in claim 14 wherein said epoxidized carboxylic acid derivative is selected from the group consisting of an epoxidized mono-, di- and tri-glyceride, and an epoxidized carboxylic acid alkyl ester containing 1 to 18 carbon atoms in the monohydric alcohol.

20. A process as in claim 14 wherein said deinking solution contains from 0 to about 1.5% by weight of 100%/wt hydrogen peroxide, from 0 to about 2.5% by weight of sodium hydroxide, from 2 to about 4% by weight of soda waterglass having a solids content of about 35%/wt, and from about 0.02 to about 2% by weight of said alkoxylated compound, based on the air-dry weight of said wastepaper.

* * * * *